(12) United States Patent
Cimino

(10) Patent No.: US 7,981,069 B2
(45) Date of Patent: Jul. 19, 2011

(54) ORTHOTIC DEVICE FOR DIABETIC PATIENTS

(76) Inventor: Salvatore Cimino, Pembroke Pines, FL (US)

( * ) Notice: Subject to any disclaimer, the term of this patent is extended or adjusted under 35 U.S.C. 154(b) by 273 days.

(21) Appl. No.: 12/473,127

(22) Filed: May 27, 2009

(65) Prior Publication Data

US 2010/0305487 A1 Dec. 2, 2010

(51) Int. Cl.
*A61F 5/00* (2006.01)
(52) U.S. Cl. ............................................. 602/23; 36/7.5
(58) Field of Classification Search .................... 602/30, 602/29
See application file for complete search history.

(56) References Cited

U.S. PATENT DOCUMENTS

| | | | |
|---|---|---|---|
| 5,464,385 A | 11/1995 | Grim | |
| 5,491,909 A | 2/1996 | Darby | |
| 6,083,185 A * | 7/2000 | Lamont | 602/65 |
| 6,945,946 B2 | 9/2005 | Rooney | |
| 7,231,728 B2 | 6/2007 | Darby | |
| RE40,363 E | 6/2008 | Grim | |
| 7,418,755 B2 | 9/2008 | Bledsoe | |

* cited by examiner

*Primary Examiner* — Stephen K Cronin
*Assistant Examiner* — Raymond Harris
(74) *Attorney, Agent, or Firm* — Ruben Alcoba, Esq.

(57) ABSTRACT

An orthotic device that minimizes weight bearing on certain areas of a shoe being worn by a diabetic suffering from a diabetic foot ulcer, the device allows patients to live active lifestyles while being treated for diabetic foot ulcerations. The orthotic device purposely establishes three points of contact between the device and a shoe. The present device is used in conjunction with a shoe having a sole that defines a cut-away wherein an ulcerous foot wound would lie.

Figure 1:
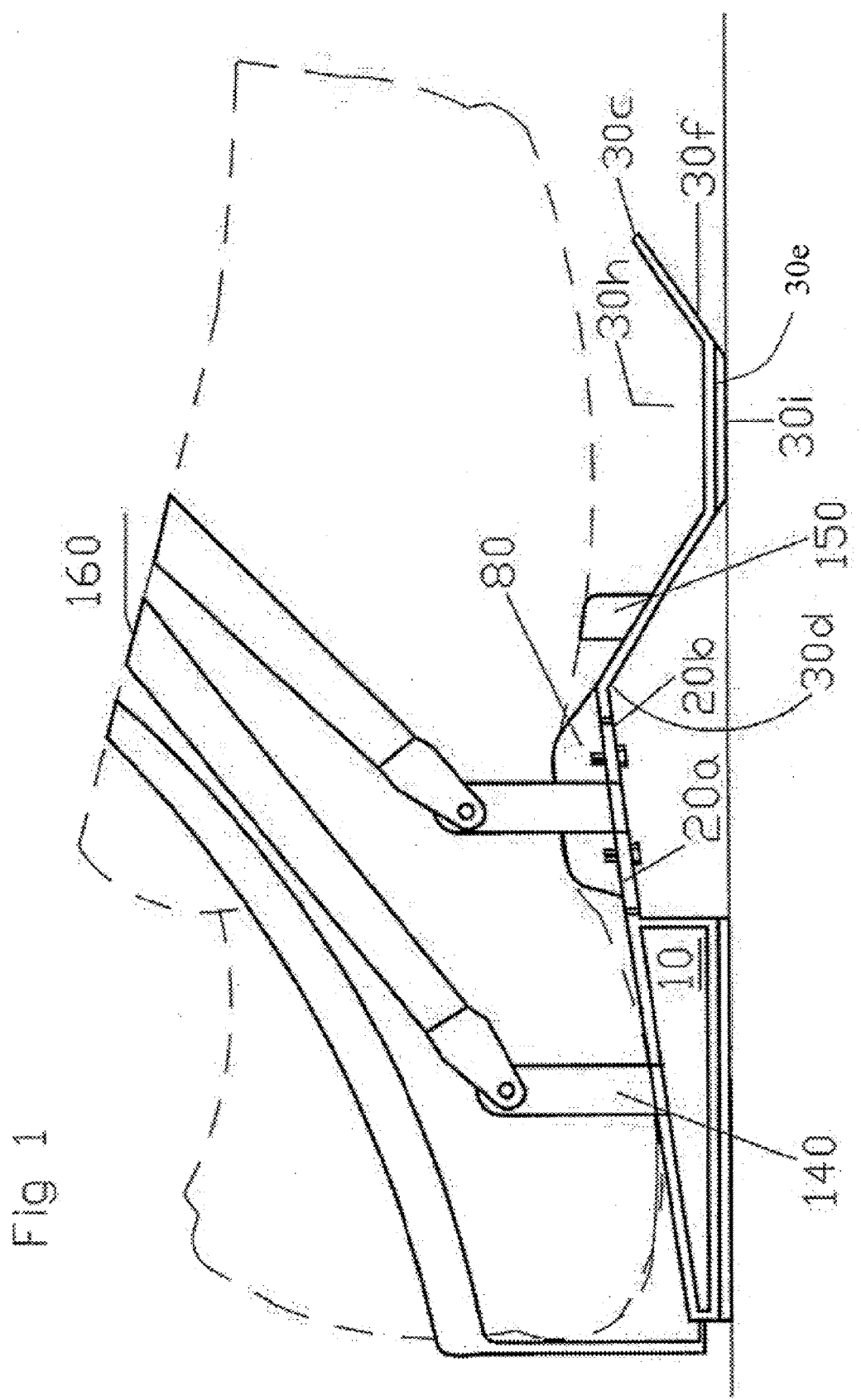

The orthotic device comprises a shoe cartridge, the shoe cartridge has a first, second and third section, each section has a left and a right side, at least five L-shaped docks attached to the shoe cartridge, a support attached to the shoe cartridge, and at least five securing means, each securing means is attached to each L-shaped dock.

3 Claims, 3 Drawing Sheets

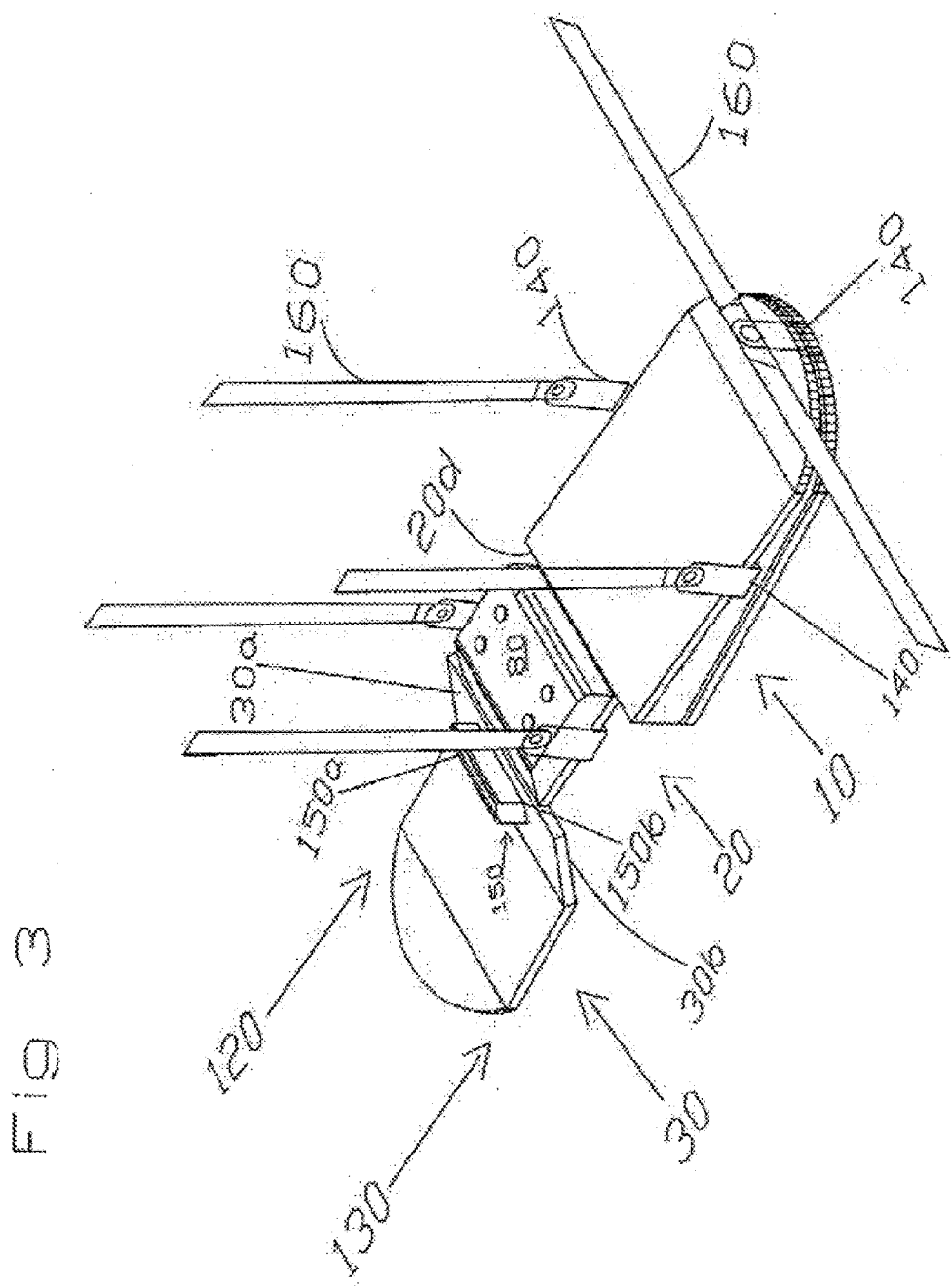

ORTHOTIC DEVICE FOR DIABETIC PATIENTS

BACKGROUND

The present invention is directed to orthopedic devices, and more particularly to orthotic support devices for assisting in the stabilization and proper healing of ulcerative conditions, especially for diabetic patients suffering from diabetic foot ulcers.

Some diabetics suffer from ulcerations, infections, and gangrene. Diabetic patients suffering from ulcerations, infections, and gangrene might require limb amputation. The present invention benefits these patients because it minimizes the pressure placed on certain areas of the plantar areas of the foot.

Many diabetics suffer from distal symmetric polyneuropathy. Distal symmetric polyneuropathy is perhaps the most common complication affecting the lower extremities of patients with diabetes mellitus. The polyneuropathy, the lack of protective sensation, combined with un-accommodated foot deformities, exposes diabetics to undue sudden or repetitive stress that leads to eventual ulcer formation with a risk of infection and possible amputation of the lower extremities.

Three basic issues need to be addressed to successfully treat diabetic foot ulcers: debridement, offloading, and infection control.

The present invention addresses the issue of offloading. Offloading is defined as the complete halting of weight bearing on an affected foot. Using the present invention, weight bearing shall be minimized to the ulcerous areas of the affected foot. At the present time, the most effective methods of offloading are through patients' use of wheelchairs or crutches.

The problem with using the above methods of offloading is that some diabetic patients are accustomed to having active lifestyles. They are used to being on the go and do not believe they have time to use wheelchairs or crutches. Some of these active individuals suffer from polyneuropathy, thus they do not experience the pain associated with the ulcers and thereby tend to not realize the damage they are causing the ulcerous areas of the foot. Eventually, some of these individuals develop wounds that are un-healable and that thereby lead to amputation of the affected areas.

Some patients treated using the methods described above almost recover fully. They do not fully recover prior to completion of treatment, because of the polyneuropathy that they suffer, they convince themselves that they are cured and continue their daily activities. By continuing their daily activities, they re-aggravate their wounds and thereby commence vicious cycles of recovery and re-aggravation that eventually lead to wounds that are un-healable.

Devices currently used to relieve pressure from ulcerated wounds include shoes having special soles that may or may not stabilize the foot. The soles define cutouts wherein ulcerated sections of the diabetic foot would lie. The problem using the above devices to treat the wounds is that the person using the shoes might sometimes step in an awkward fashion and thereby dislodge the foot from a first position, the position being where the wound would be within the cutout, to a second position, wherein the wound would be displaced from the Cutout section of the sole to a solid position of the sole. When the foot is in the second position, the patient being treated would aggravate the wound.

The inventor of the present invention suffers from diabetic foot ulcers and has invented a universal device that is to be worn on the exterior of most shoes. The device will have three points of contact with existing shoes. Most shoes have two major points of contact with the ground, the heel and the pad of the shoe. The present invention purposely establishes three points of contact between the shoe and the device. By establishing the third point of contact, the device shifts the weight from two specific points of contact to three points of contact. By creating a third point of contact, a specific section of a point of contact of the heel or the pad will be avoided.

The design of the device allows a wounded section of the a foot to be securely stabilized within a shoe while avoiding a specific point of contact between the shoe and the device. The shoe mounted on the device would ideally use a sole that would have a cutout for the ulcer to lie in. The section of the shoe having the cutout is prevented from bearing weight because of the device. The reason for this is that the section of the shoe having the cutout would be elevated by the three points of contact of the present invention.

For the foregoing reasons, there is a need for an orthotic device that minimizes weight bearing on certain areas of a shoe being worn by a diabetic suffering from a diabetic foot ulcer that will allow the patients to live active lifestyles while being treated for foot ulcerations.

SUMMARY

The present invention is directed to orthotic devices that minimize weight bearing on certain areas of a shoe being worn by a diabetic suffering from a diabetic foot ulcer, the device allows patients to live active lifestyles while being treated for diabetic foot ulcerations. The orthotic device purposely establishes three points of contact between the device and a shoe. The three points of contact of the device minimize the chances that an ulcer on the bottom of a foot of a wearer would make contact with a surface of the shoe being worn by the wearer. The present device is used in conjunction with a shoe having a sole that defines a cutaway wherein an ulcerous foot wound would lie.

The orthotic device for diabetic patients comprises a shoe cartridge, the shoe cartridge has a first, second and third section, each section has a left and a right side, at least five L-shaped docks attached to the shoe cartridge, a support attached to the shoe cartridge, and at least five securing means, each securing means is attached to each L-shaped dock.

The orthotic device is used by placing a shoe (the shoe having a heel, a middle, and a pad section) being worn by a user suffering from a diabetic foot ulcer within the orthotic device so that the heel section is positioned over the first section of the shoe cartridge of the device, the middle section of the shoe is over the second section of the shoe cartridge of the device, and the pad section of the shoe is over the support of the device. Then securing the securing means of the shoe around the shoe being worn by the user.

An object of the present invention is to provide an orthotic device that will allow a user of the device to live an active lifestyle while being treated for a diabetic foot ulcer.

Another object of the present invention is to provide an orthotic device that will allow a user of the device to wear the device with the security that he will not aggravate the diabetic foot ulcer when wearing the device.

A further object of the present invention is to allow a user of the orthotic device to use the device without calling much attention to himself, thereby increasing the user's self confidence.

Still a further object of the present invention is to minimize amputations of limbs due to diabetic foot ulcers.

Yet a further object of the present invention is to provide an orthotic device that will allow a diabetic foot ulcer to heal completely, thereby preventing a cycle of diabetic foot ulceration.

DRAWINGS

Figure 2:
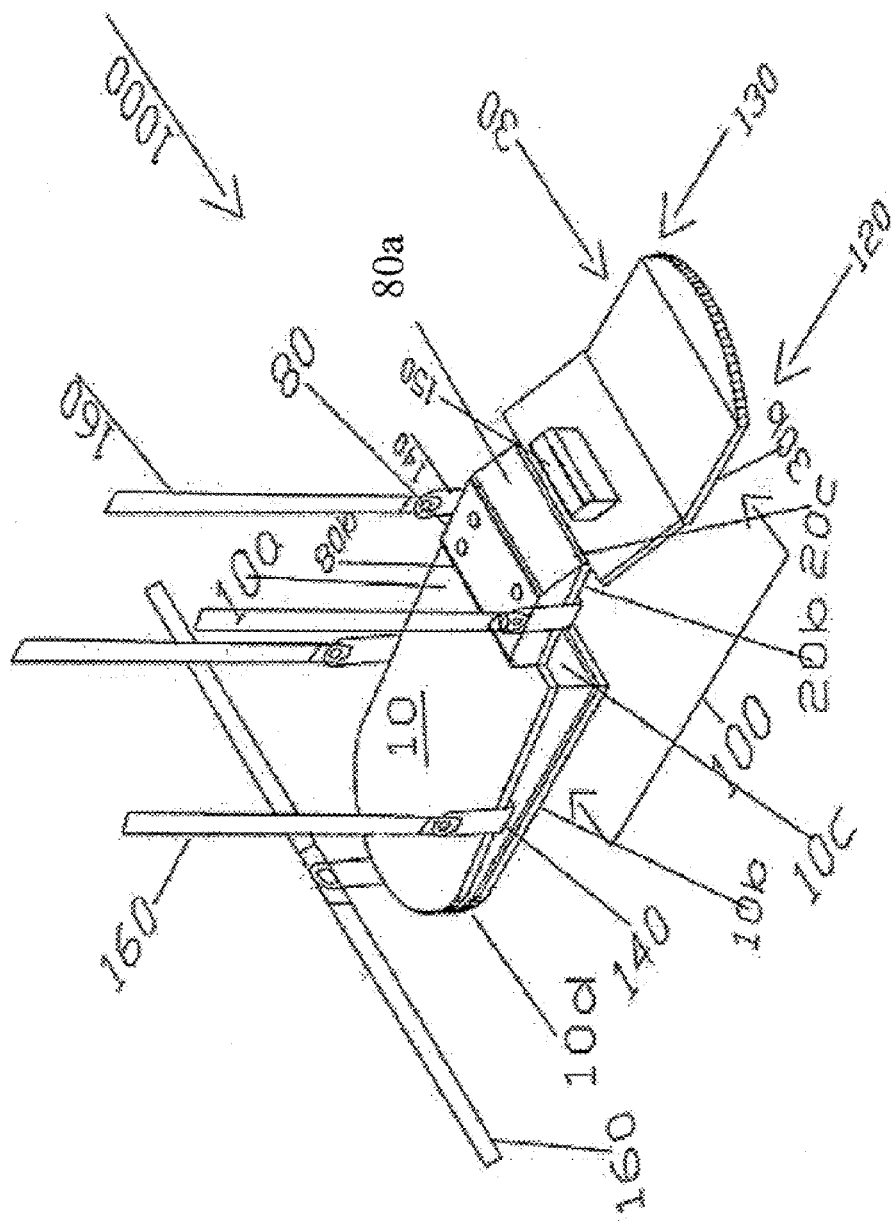

These and other features, aspects, and advantages of the present invention will become better understood with regard to the following description, appended claims, and drawing where:

FIG. 1 is a side view of an orthotic device that minimizes weight bearing on certain areas of a shoe being worn by a diabetic suffering from a diabetic foot ulcer, the Figure shows a shoe mounted on the device, the shoe is not part of the device and is shown only to show how a shoe would be mounted and secured on the device;

FIG. 2. Shows a right side view of the orthotic device; and

FIG. 3. shows a left side view of the orthotic device.

DESCRIPTION

As seen in FIGS. 1-3, an orthotic device 1000 that minimizes weight bearing on certain areas of a shoe being worn by a diabetic suffering from a diabetic foot ulcer, the orthotic device comprises a shoe cartridge 100, the shoe cartridge 100 has a first 10, second 20 and third 30 section, each section has a left 130 and a right 120 side, at least five L-shaped docks 140 attached to the shoe cartridge 100, a support 150 attached to the shoe cartridge 100, and at least five securing means 160, each securing means 160 is attached to each L-shaped dock 140.

The shoe cartridge's 100 first section 10 has a top 10a, a bottom 10b, a proximal 10c and a distal side 10d, and the top 10a and the bottom 10b sides are substantially planar, the bottom side 10b of the first section 10 of the shoe cartridge 100 being in a certain plane, the top side 10a rising from the bottom side 10b at an angle of at least five to at most thirty degrees upward toward the second section 20 of the shoe cartridge 100. The second section 20 of the shoe cartridge 100 has a top 20a, a bottom 20b, a proximal 20c and a distal side 20d. The top side 20a of the second section 20 of the shoe cartridge 100 runs flush with the top side 10a of the first section 10 of the shoe cartridge 100 and the top side 20a of the second section 20 of the shoe cartridge 100 has a protrusion 80 that rises upward from at least one-eighth of an inch to at most three-fourths of an inch from the top side 20a of the second section 20 of the shoe cartridge 100, the protrusion 80 has a proximal 80a and a distal 80b side. The third section 30 has a top 30a, a bottom 30b, a proximal 30c and a distal side 30d, and a middle section 30e. The distal side 30d of the third section 30 of the shoe cartridge 100 runs downward toward the middle section 30e of the third section 30 of the shoe cartridge 100 at a downward angle of at least twenty degrees to at most sixty degrees with relation to the certain plane of the first section 10 of the shoe cartridge 100. The middle section 30e of the third section 30a has a top 30h, a bottom 30i, a proximal 30f, and a distal 30g side, the bottom side 30i of the middle section 30e of the third section 30 is in the same plane as the bottom side 10b of the first section 10 of the shoe cartridge 100 and the bottom side 30i of the middle section of the third section 30 of the shoe cartridge 30 measures from at least two and a half inches to at most six inches in length when measured from the bottom side 30g of the distal side to the proximal side 30f of the middle section 30e of the third section 30 of the shoe cartridge 100. The proximal side 30f of the middle section 30e of the third section 30 of the shoe cartridge 100 plane might rise upward from the bottom side 30i of the middle section 30e at an angle from at least twenty degrees to at most forty-five degrees with relation to the certain plane of the first section 10 of the shoe cartridge 100.

The L-shaped docks 140 attach to the first section 10 of the shoe cartridge so that a first L-shaped dock 140 is centrally positioned on the distal end 10d of the first section 10 of the shoe cartridge 100, a second L-shaped dock 140 is centrally positioned on the right side 120 of the first section 10 of the shoe cartridge 100, a third L-shaped dock 140 is centrally positioned on the right side 120 of the second section 20 of the shoe cartridge 100, a fourth L-shaped dock 140 is centrally positioned on the left side 130 of the first section 10 of the shoe cartridge 100, and a fifth L-shaped dock 140 is centrally positioned on the left side 130 of the second section 20 of the shoe cartridge 100, all of the L-shaped docks 140 rise at a ninety degree angle in relation to the certain plane of the bottom of the first section 10b of the shoe cartridge 100.

The support 150 has a top 150a and a bottom side 150b, the bottom side 150b of the support 150 attaches to the top side 30e of the third section 30 of the shoe cartridge 100 so that it is attached at a position that supports a shoe worn by a user suffering from a diabetic foot ulcer in a manner that prevents the user's weight to be applied to the area of the user's ulcer.

The five securing means 160 attach as follows: the first securing means 160 attaches to itself, the second 160 and fourth 160 securing means attach to each other, and the third 160 and fifth securing 160 means attach to each other. All of the securing means 60 attach as described after a shoe is secured with the orthotic device. The securing means 160 might be made of hook and loop materials or might be simple shoe strings.

In an embodiment of the present invention, the first 10 and third 30 sections of the shoe cartridge 100 will further comprise of a non-slip pad 12 attached to the bottom side of each section 10, 30 of the shoe cartridge.

The orthotic device 1000 is used as follows: first providing the orthotic device 1000, providing a user having foot having a diabetic foot ulcer, and providing a shoe, the shoe having a heel, a middle, and a pad section, the shoe having a cutout wherein the foot of the diabetic will be placed so that the diabetic foot ulcer will lie within the cutout; then, placing the shoe worn by the user within the orthotic device 1000 so that the heel section of the shoe is positioned over the first section 10 of the shoe cartridge 100 of the orthotic device 100, the middle section of the shoe is over the protrusion 80 of the second section 20 of the shoe cartridge 100 of the orthotic device 1000, and the pad section of the shoe is over the support 150 of the orthotic device 1000; and lastly, securing the securing means 160 of the orthotic device 1000 around the shoe being worn by the user.

An advantage of the present invention is that it provides an orthotic device that allows a user of the device to live an active lifestyle while being treated for a diabetic foot ulcer.

Another advantage of the present invention is that it provides an orthotic device that allows a user of the device to wear the device with the security that he will not aggravate the diabetic foot ulcer when wearing the device.

A further advantage of the present invention is that it allows a user of the orthotic device to use the device without calling much attention to himself, thereby increasing the user's self confidence.

Still a further advantage of the present invention is that it minimizes amputations of limbs due to diabetic foot ulcers.

Yet a further advantage of the present invention is that it provides an orthotic device that allows a diabetic foot ulcer to heal completely, thereby preventing a cycle of diabetic foot ulceration.

Although the present invention has been described in considerable detail with reference to certain preferred versions thereof, other versions are possible. Therefore the spirit and the scope of the claims should not be limited to the description of the preferred versions contained herein.

What is claimed is:

1. An orthotic device that minimizes weight bearing on certain areas of a shoe being worn by a diabetic suffering from a diabetic foot ulcer, the orthotic device comprises a shoe cartridge, the shoe cartridge has a first, second and third section, each section has a left and a right side, at least five L-shaped docks attached to the shoe cartridge, a support attached to the shoe cartridge, and at least five securing means, each securing means is attached to each L-shaped dock:

wherein the shoe cartridge's first section has a top, a bottom, a proximal and a distal side, the top and the bottom sides being substantially planar, the bottom side of the first section of the shoe cartridge is in a certain plane, the top side rising from the bottom side at an angle between five to thirty degrees upward toward the second section of the shoe cartridge;

wherein the second section of the shoe cartridge has a top, a bottom, a proximal and a distal side, the top side of the second section of the shoe cartridge runs flush with the top side of the first section of the shoe cartridge and the top side of the second section of the shoe cartridge has a protrusion that rises upward from at least one-eighth of an inch to at most three-fourths of an inch from the top side of the second section of the shoe cartridge, the protrusion has a proximal and a distal side;

wherein the third section has a top, a bottom, a proximal and a distal side, and a middle section, the distal side of the third section of the shoe cartridge runs downward toward the middle section of the third section of the shoe cartridge at a downward angle of at least twenty degrees to at most sixty degrees with relation to the certain plane of the first section of the shoe cartridge, the middle section of the third, section has a top, a bottom, a proximal, and a distal side, the bottom side of the middle section of the third section is in the same plane as the bottom side of the first section of the shoe cartridge and the bottom side of the middle section of the third section of the shoe cartridge measures from at least two and a half inches to at most six inches in length when measured from the bottom side of the distal side to the proximal side of the middle section of the third section of the shoe cartridge;

wherein the L-shaped docks attach to the first section of the shoe cartridge so that a first L-shaped dock is centrally positioned on the distal end of the first section of the shoe cartridge, a second L-shaped dock is centrally positioned on the right side of the first section of the shoe cartridge, a third L-shaped dock is central positioned on the right side of the second section of the shoe cartridge, a fourth L-shaped dock is centrally positioned on the left side of the first section of the shoe cartridge, and a fifth L-shaped dock is centrally positioned on the left side of the second section of the shoe cartridge, all of the L-shaped docks rise at a ninety degree angle in relation to the certain plane of the bottom of the first section of the shoe cartridge;

wherein the support has a top and a bottom side, the bottom side of the support attaches to the top side of the third section of the shoe cartridge so that it is attached at a position that supports a shoe worn by a user suffering from a diabetic foot ulcer in a manner that prevents the user's weight to be applied to the area of the user's ulcer; and wherein the five securing means attach as follows: the first securing means attaches to itself, the second and fourth securing means attach to each other, and the third and fifth securing means attach to each other, all of the securing means attach as described after a shoe is secured with the orthotic device.

2. The orthotic devise of claim 1, wherein the proximal side of the middle section of the third section of the shoe cartridge plane rises from the bottom side of the middle section at an angle from at least twenty degrees to at most sixty degrees.

3. A method of using the orthotic device of claim 1, comprising the steps of:

providing the orthotic device for use by a user wherein the user has a diabetic foot ulcer;

providing a shoe, the shoe having a heel, a middle, and a pad section, the shoe having a cutout wherein the foot of the diabetic will be placed so that the diabetic foot ulcer will lie within the cutout;

then, placing the shoe worn by the user within the orthotic device so that the heel section of the shoe is positioned over the first section of the shoe cartridge of the orthotic device, the middle section of the shoe is over the protrusion of the second section of the shoe cartridge of the orthotic device, and the pad section of the shoe is over the support of the orthotic device; and lastly, securing the securing means of the orthotic device around the shoe being worn by the user.

\* \* \* \* \*